United States Patent
Boltz et al.

(10) Patent No.: US 8,844,094 B2
(45) Date of Patent: Sep. 30, 2014

(54) MULTI-PORT PROBE PURGE SYSTEMS AND TECHNIQUES

(75) Inventors: Eric S. Boltz, West Chester, OH (US); Justin Matthew Clark, West Chester, OH (US)

(73) Assignee: United Process Control Inc., Dover, DE (US)

( * ) Notice: Subject to any disclaimer, the term of this patent is extended or adjusted under 35 U.S.C. 154(b) by 801 days.

(21) Appl. No.: 12/490,831

(22) Filed: Jun. 24, 2009

(65) Prior Publication Data
US 2009/0320888 A1    Dec. 31, 2009

Related U.S. Application Data

(60) Provisional application No. 61/075,660, filed on Jun. 25, 2008.

(51) Int. Cl.
*B08B 9/02* (2006.01)
*G01N 33/00* (2006.01)

(52) U.S. Cl.
CPC ........ *G01N 33/0029* (2013.01); *G01N 33/0006* (2013.01)
USPC ........................................... 15/405; 15/316.1

(58) Field of Classification Search
USPC ............ 15/405, 56, 104.1, 104.2, 104.5, 246, 15/345, 363, 383, 395, 316.1, 317, 318, 15/330; 134/8, 10, 21, 22.11, 22.12, 166 R, 134/166 C, 167 R, 167 C
See application file for complete search history.

(56) References Cited

U.S. PATENT DOCUMENTS

| | | | | |
|---|---|---|---|---|
| 4,290,586 A | * | 9/1981 | Kane et al. | 266/80 |
| 4,362,580 A | * | 12/1982 | Kane et al. | 148/508 |
| 5,109,562 A | * | 5/1992 | Albrecht | 15/56 |
| 5,324,415 A | * | 6/1994 | Blumenthal et al. | 204/427 |
| 5,851,369 A | * | 12/1998 | Cai | 204/428 |
| 6,093,295 A | * | 7/2000 | Zhuiykov et al. | 204/427 |
| 2003/0084728 A1 | * | 5/2003 | Boltz | 73/753 |

FOREIGN PATENT DOCUMENTS

| | | |
|---|---|---|
| JP | 2005537926 | 12/2005 |
| JP | 2006167672 | 6/2006 |
| JP | 3836419 | 10/2006 |
| WO | WO-2009158400 A1 | 12/2009 |

OTHER PUBLICATIONS

"Application Serial No. PCT/US2009/048444, International Preliminary Report on Patentability mailed Jan. 13, 1111", 8 pgs.

(Continued)

*Primary Examiner* — Dung Van Nguyen
(74) *Attorney, Agent, or Firm* — Schwegman Lundberg & Woessner, P.A.

(57) ABSTRACT

Tubes are used to perform a focused cleaning of a sensor tip. By surrounding the tip with burn-off "jets," the tip is invariably cleaned by a purge procedure even when strong atmosphere currents are present in a furnace. In dirty environments, an additional purge port, without a focused tube, is used to ensure cleaning of the upper portion of the sheath to prevent soot causing seizure of a sensor element. Alternatively, a means for saturating a sensor's active element with cleaning air is provided, such that a single tube directs air into a multi-port ring at a sensor's tip or into the tip of a sheath, which has channels/holes directing air for purposes of saturating the tip from multiple directions.

15 Claims, 11 Drawing Sheets

(56) References Cited

OTHER PUBLICATIONS

"International Application Serial No. PCT/US2009/048444, Search Report mailed Oct. 30, 2009", 4 gps.

"International Application Serial No. PCT/US2009/048444, Written Opinion mailed Oct. 30, 2009", 6 pgs.

* cited by examiner

MULTI-PORT PROBE PURGE SYSTEMS AND TECHNIQUES

RELATED APPLICATIONS

The present application is a Non-Provisional Application of and claims priority to U.S. Provisional Application No. 61/075,660, entitled "Multi-Port Purge System," filed on Jun. 25, 2008; the disclosure of which is hereby incorporated in its entirety by reference herein and below.

BACKGROUND

Sensors used in dirty environments often require regular cleaning. For example, oxygen sensors used in carburizing furnaces must frequently be purged (or in industry terms "burned off") to remove soot buildup from the process.

The traditional means for purging such sensors is to flow air into the space between the sensor's protective outer sheath and its inner sensor element until that air saturate the tip (active sensor element) and burns the soot deposits.

This process can take significant time (1-2 minutes) and the sensor takes up to thirty minute to recover and read correctly again owing to the large build-up of air or within the probe sheath.

Previously, techniques used a "focused" burn-off design. In this design, a single small tube carried the burn-off air directly to the tip of the probe. The techniques dramatically reduced the volume of air needed to saturate the tip, thereby cleaning it.

Consequently, improved sensor purge systems are needed.

SUMMARY

In various embodiments, multi-port probe purge systems and techniques are presented. More specifically, and in an embodiment, a multi-port probe purge system is provided for sensor cleaning. The multi-port probe purge system includes multiple ports configured to surround a tip of a sensor and the sensor. The multiple ports are further configured to deliver air at the tip of the sensor to purge soot accumulated at the tip of the sensor from operation of the sensor.

DETAILED DESCRIPTION

Embodiments of the invention include multiple tubes that are used to perform a focused cleaning of the sensor tip. By surrounding the tip with burn-off "jets" the tip is invariably cleaned by a purge procedure even when strong atmosphere currents are present in a furnace.

In very dirty environments an additional purge port, without a focused tube, is used to ensure cleaning of the upper portion of the sheath to prevent soot causing seizure of the sensor element, though this is not likely necessary for most applications.

Alternate Embodiments

Other means for saturating the sensor's active element with cleaning air include a single tube that directs air into a multi-port ring at the sensor's tip or into the tip of the sheath which has been designed with channels or holes to direct the air in such a manner as to saturate the tip from multiple directions.

Variations

Same or similar designs for introducing calibration gases (also called zero and span gases) into gas sensors or analyzers. Many sensors require calibration using specific value gases (calibration gas) and gas with no target species (zero gas). Like burn-off, the typical technique is to flood the sheath or use a single small tube to focus the gas on the sensor's active element. However with the approaches discussed herein, a multi-port means for introducing such gases such that the tip is saturated even in high-flow environments.

Sensor Burnoff

A carbon sensor operates in a very harsh environment where carbon deposits (soot) often form on the sensor. As soot accumulates at the tip of the sensor, the sensing surface of the sensor is shielded from the furnace atmosphere. This results in false, elevated carbon readings which cause the controller to reduce the flow of enriching gas, resulting in low carbon or decarburizing conditions.

This effect is amplified in processes using elevated carbon set points such as boost and diffuse carburizing. Additionally, the high nickel content in the protective sheath alloy, while adding resistance to high temperatures, also acts as a catalyst, accelerating the deposit of carbon on the sheath.

Fact: Over 80% of carbon probe electrode failures are due to excessive carbon buildup at the outer electrode.

Fortunately, removal of carbon deposits can be achieved by running air through the "Burnoff" fitting supplied on carbon probes.

Self-cleaning of carbon probes using air burnoff of accumulated carbon can be done successfully if the variables involved in the process are understood. The following items all contribute to the process, in order of importance:

1) amount of air added for burnoff;
2) atmosphere circulation around the probe; and
3) location and amount of carbon that has accumulated.

Figure 1:
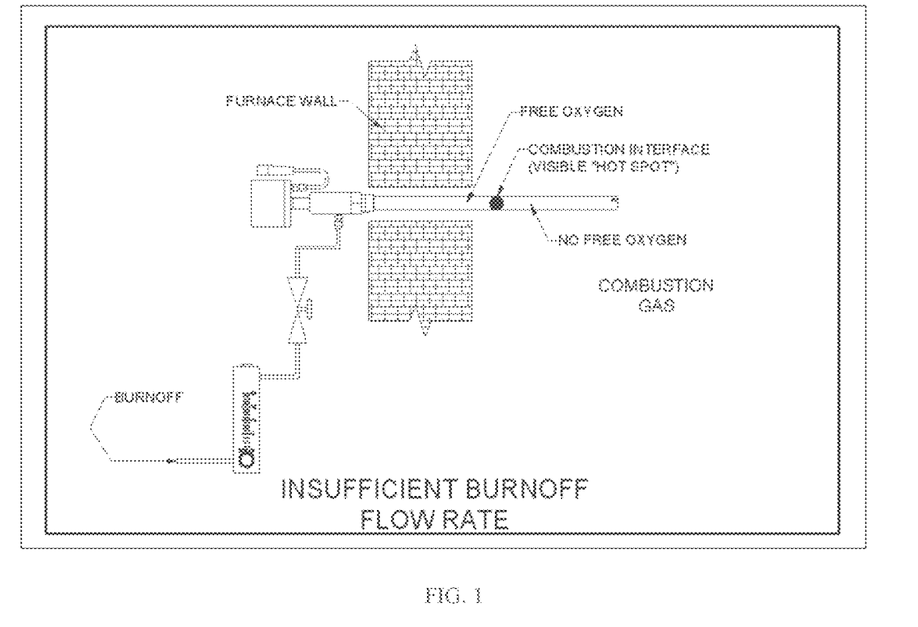
FIG. 1 is a diagram illustrating insufficient burnoff flow rate when air is forced into a probe sheath.

When air is forced into the probe sheath FIG. 1 a combustion reaction between the air and the furnace atmosphere takes place. The location of this reaction naturally settles at some equilibrium location. In some furnaces, it is possible to see exactly where this reaction is taking place by watching the probe sheath during burnoff. A "hot spot" marks the location.

Figure 2:
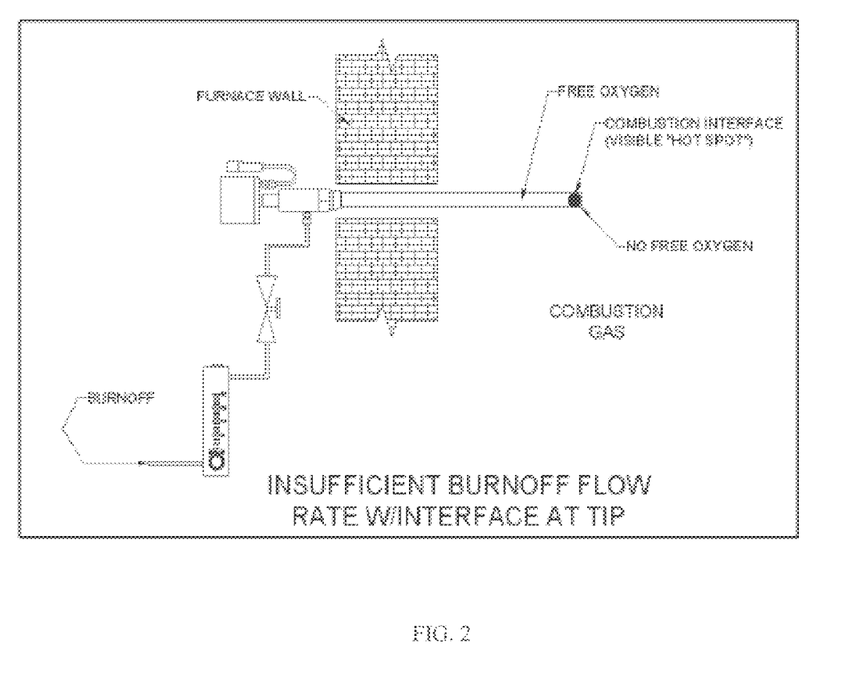
FIG. 2 is a diagram illustrating insufficient burnoff flow rate when air is forced into a probe sheath with an interface at a tip of the sheath.
Figure 3:
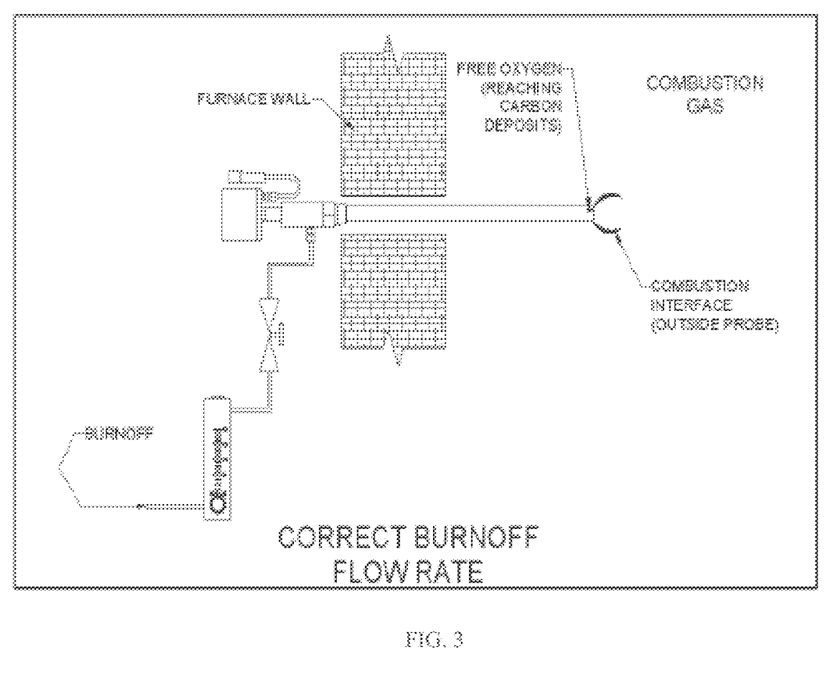
FIG. 3 is a diagram illustrating a correct or sufficient burn off flow rate when air is forced into a probe sheath.

As the amount of air is changed, the location of the combustion interface can be changed. The higher the air flow, the further out in the probe sheath the interface moves (FIG. 2). If enough air is added, the combustion reaction can actually be moved completely outside of the probe (FIG. 3).

Note that the atmosphere in front of the interface does not contain significant amounts of free oxygen while the atmosphere behind the interface does. Removal of solid carbon is much more efficient if free oxygen is present to react with it. This means that enough air should be used to push the combustion interface at least to the probe electrode and preferably slightly beyond. To judge the free oxygen level, it is necessary to interpret the probe mV output. For example, at 1700° F., the following values apply:

TABLE 1

| $O_2$ mV | % $O_2$ |
|---|---|
| 1150 | $9.9 \times 10^{-19}$ |
| 700 | $3.6 \times 10^{-11}$ |
| 100 | .43 |

A lower mV reading from the probe indicates how much burnoff air is reaching the tip. The mV will never reach a 0 mV level with process atmosphere present but it should drop significantly.

The amount of air required in a given installation depends heavily on the amount of circulation of furnace atmosphere around the probe. The higher the circulation velocity, the more air is required to get the interface out to the probe tip. One example noted that 20 CFH (9400 cc/min) was not enough to overcome the atmosphere circulation, yet when the furnace fan was shut off, less than 2 CFH (950 cc/min) was found to be adequate.

When the combustion reaction (burnoff) is centered at the probe tip, a rise of as much as 200° F. may be observed in the probe thermocouple (T/C). Care must be taken to keep the probe tip below 1850°, or permanent damage may result. Determination of the required flow rate of burnoff air is estimated by plotting the flow rate of air versus the sensor's mV reading.

Figure 4:
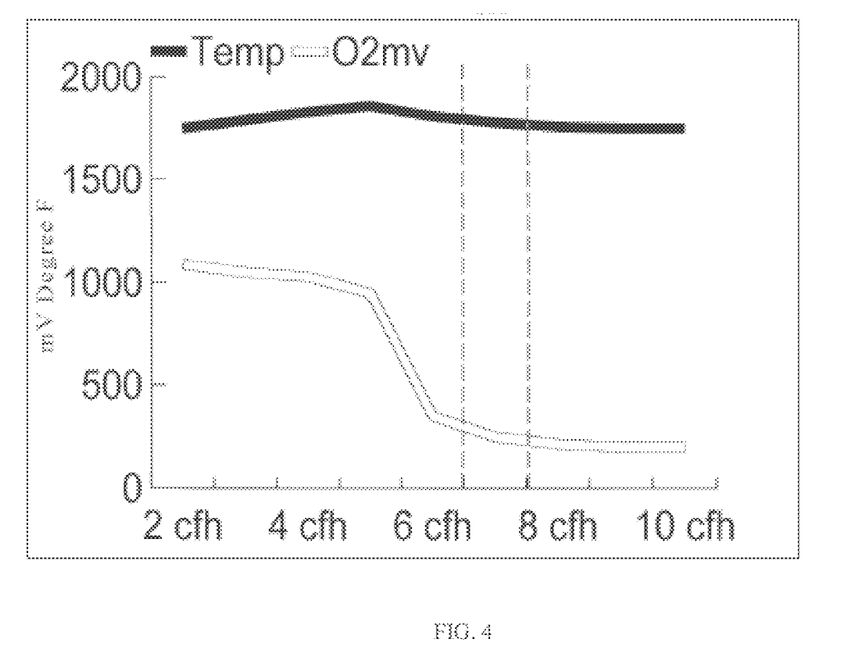
FIG. 4 is a graph diagram for an example set of data depicting a flow rate of air required for burnoff.

FIG. 4 shows a typical example of data used to determine the flow rate of air required for burnoff. In this situation, a flow rate of 7-8 CFH would be selected because this provides a lower temperature as well as some free oxygen at the probe tip. If the amount of air required is found to be so high that interference with product processing is anticipated, the probe should be relocated to a spot that will offer less impingement from the atmosphere circulation system.

For the Value line of sensors, the Magnum line of sensors (excluding Ceramic Magnum), the Headless-LT sensor, and Carbonseer-M burnoff duration should be between 60-180 seconds (1-3 minutes). All other probes should have a burnoff length between 120-300 seconds (2-5 minutes). Do not let the probe temperature rise above its maximum allowable temperature. The frequency of the operation depends upon the rate at which carbon is being accumulated. In continuous furnace applications, the burnoff process is run 3-6 times daily, while in batch applications, the burnoff should be done at the start of each cycle. To verify the effectiveness of the burnoff procedure, remove the probe after a burnoff and examine it.

The multi-port probe purge systems of the present invention consolidate mechanical components. The single alumina tube eliminates the need for smaller tubes and still accomplishes the multi-port focused purge presented herein.

A typical burn-off requires longer duration to achieve adequate results. A typical burn-off cycle does not completely remove build up from the tip of the sensor. The multi-port burn-off probe embodiments of the present invention alleviates this inefficiency by focusing the burn-off air on the tip.

Figure 5:
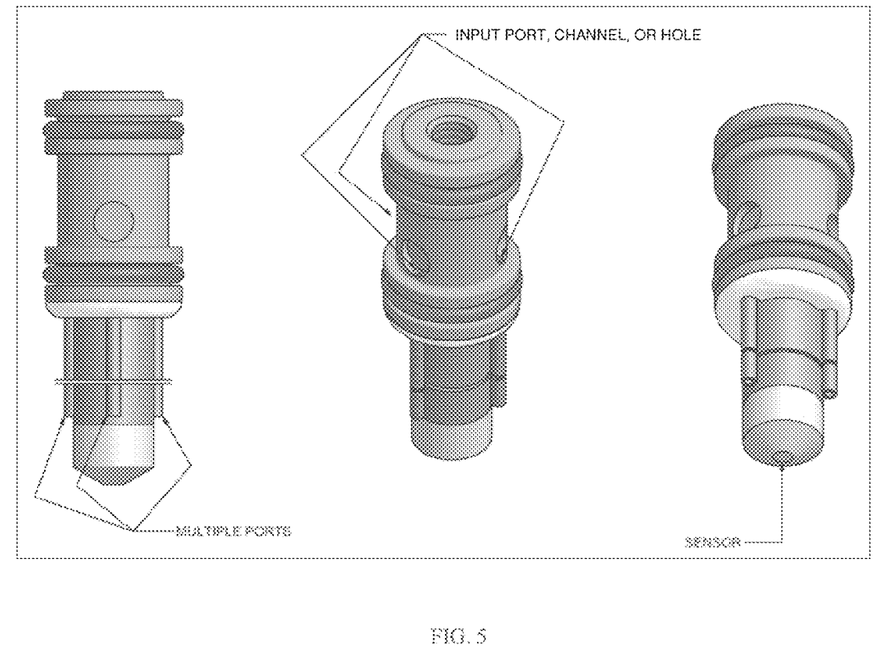
FIG. 5 is a diagram illustrating a multi-port probe burnoff system, according to an example embodiment of the invention.
Figure 6:
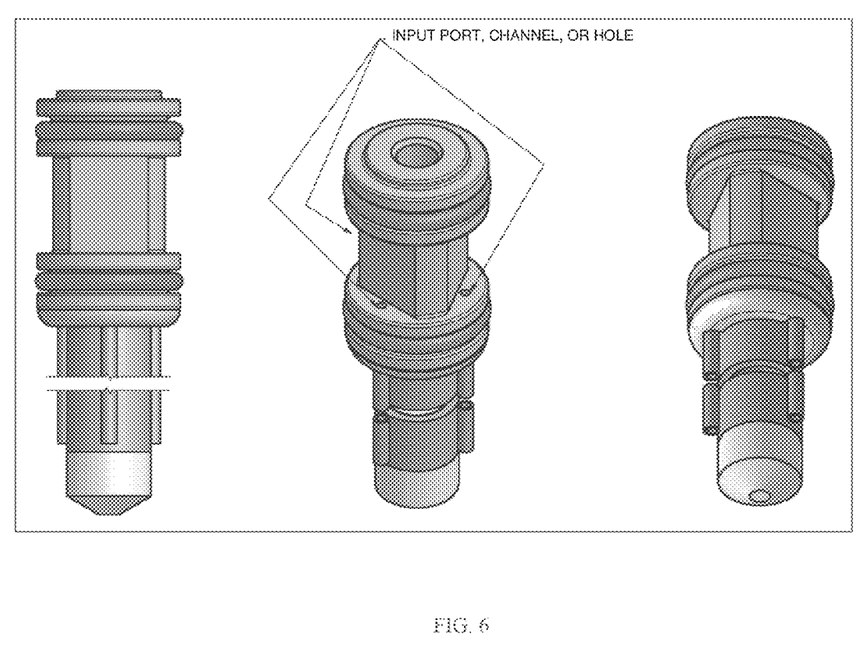
FIG. 6 is a diagram illustrating another multi-port probe burnoff system, according an example embodiment of the invention.
Figure 7:
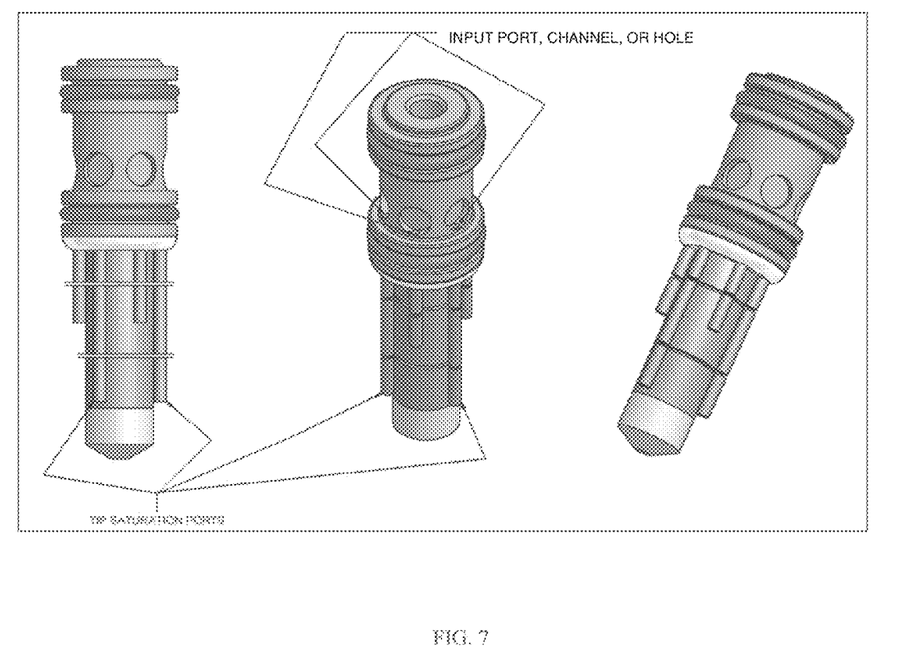
FIG. 7 is a diagram illustrating still another multi-port probe burnoff system, according an example embodiment of the invention.
Figure 8:
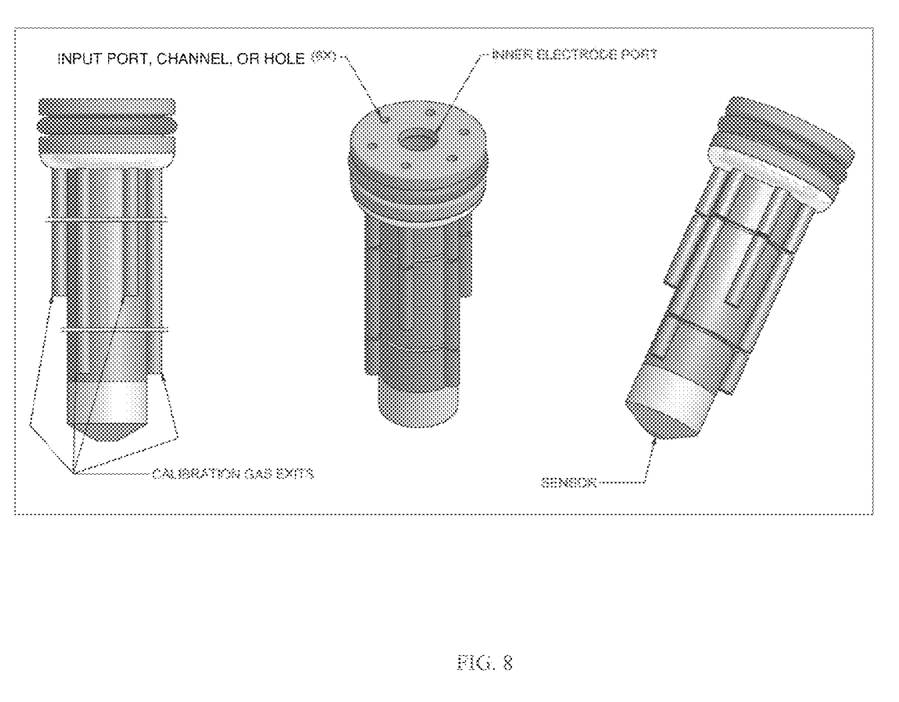
FIG. 8 is a diagram illustrating yet another multi-port probe burnoff system, according an example embodiment of the invention.
Figure 9:
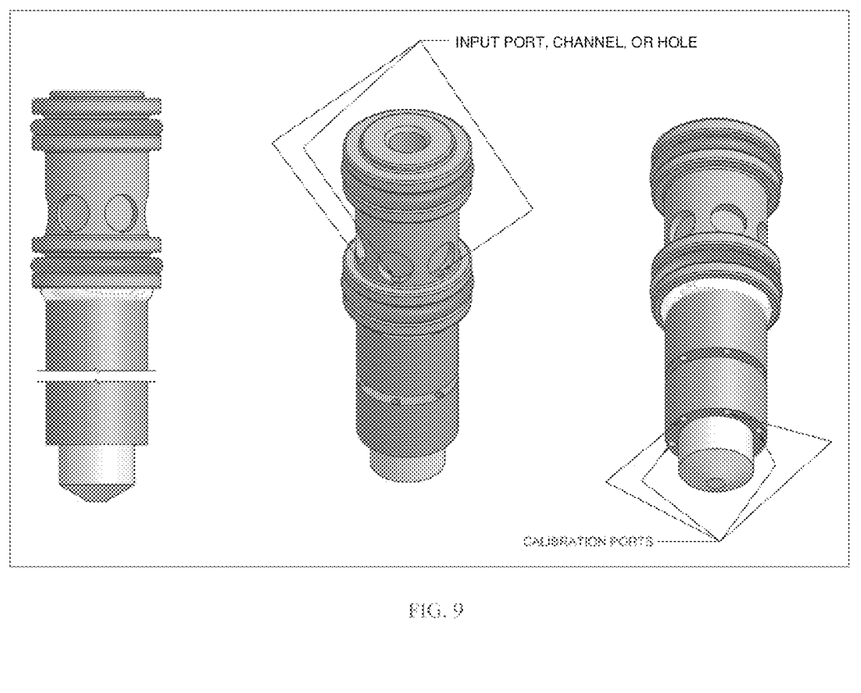
FIG. 9 is a diagram illustrating another multi-port probe burnoff system, according an example embodiment of the invention.
Figure 10:
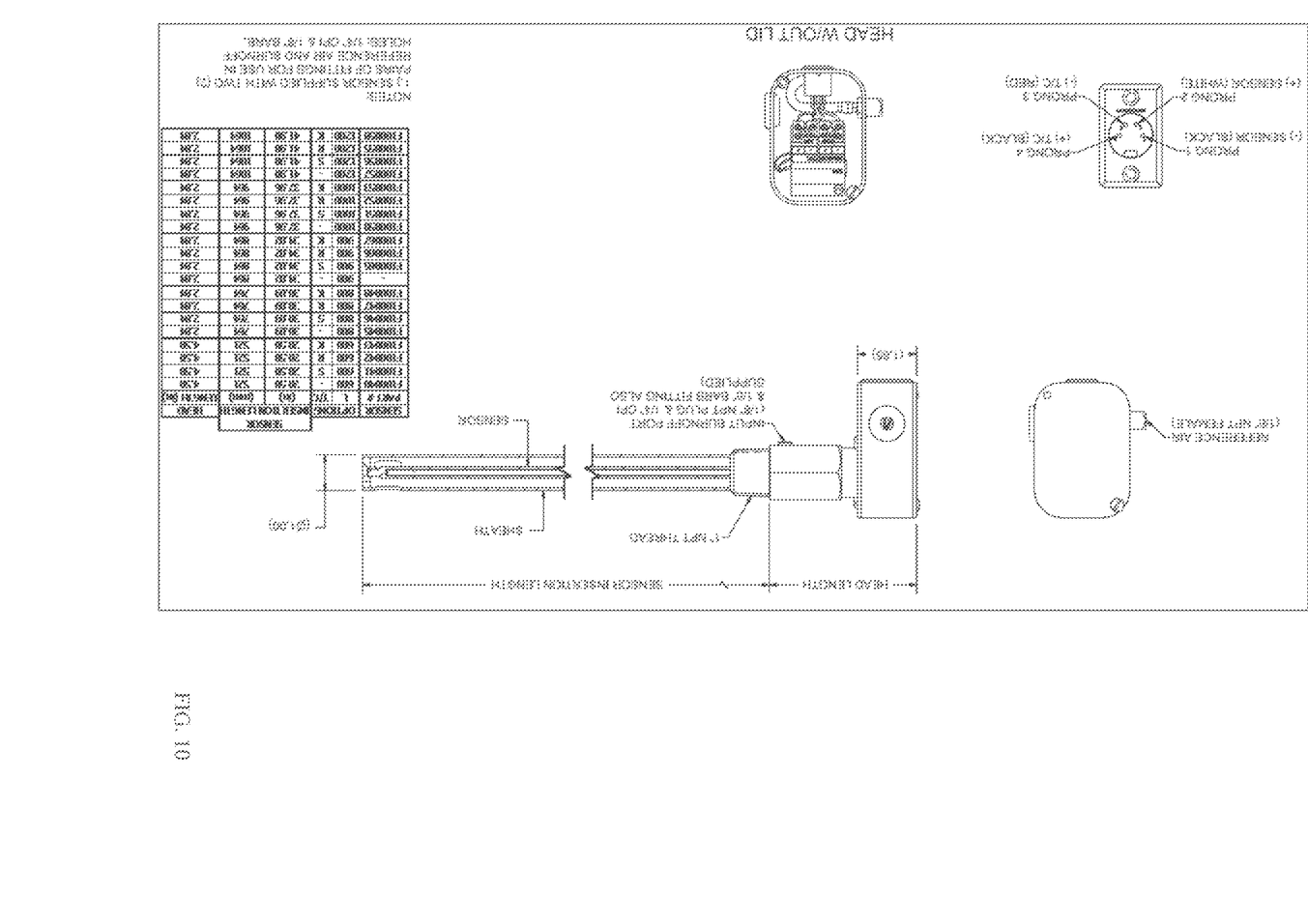
FIG. 10 is a diagram illustrating example detail for a sensor with burnoff port, according to an example embodiment of the invention.
Figure 11:
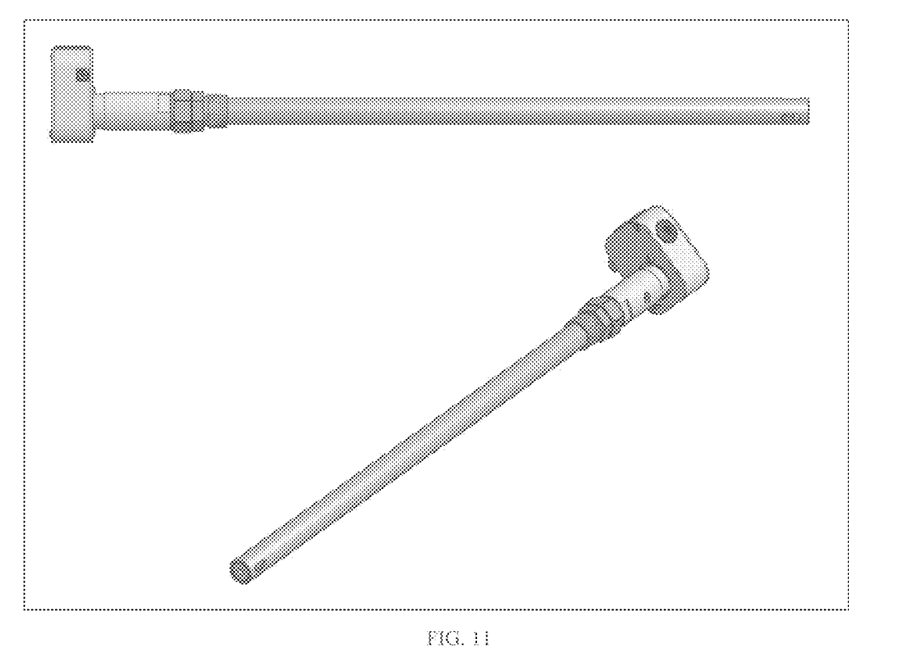
FIG. 11 is a diagram illustrating example views of a sensor with burnoff port, according to an example embodiment of the invention.

Illustrative embodiments of the multi-port probe purge system are presented in FIGS. 5-11. Specifically, FIGS. 5-6 show a 3-port probe purge system, according to example embodiments of the invention. FIGS. 7-9 show a 6-port probe purge system, according example embodiments of the invention. FIG. 10 shows some example detail of a sensor and a multi-port probe burnoff, according to an example embodiment. FIG. 11 shows two-different views of a sensor with multi-port probe burnoff.

The above description is illustrative, and not restrictive. Many other embodiments will be apparent to those of skill in the art upon reviewing the above description. The scope of embodiments should therefore be determined with reference to the appended claims, along with the full scope of equivalents to which such claims are entitled.

The Abstract is provided to comply with 37 C.F.R. §1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Description of the Embodiments, with each claim standing on its own as a separate exemplary embodiment.

The invention claimed is:

1. A multi-port probe calibration system, comprising:
multiple ports configured to surround a tip of a sensor and emit calibration gases; and
the tip of the sensor saturated with the calibration gases from the multiple ports to calibrate the sensor.

2. The system of claim 1, wherein the multiple ports include 3 ports.

3. The system of claim 1, wherein the multiple ports include 6 ports.

4. The system of claim 1, wherein the multiple ports are arranged as ring, each port forming a channel or a hole and the multiple channels or holes surrounding the tip from multiple directions for purposes of saturating the calibration gases at the tip of the sensor from the multiple directions.

5. The system of claim 1 further comprising, an additional port separate from the multiple ports and not focused on the tip, the additional port configured to use air ejected through the multiple ports for cleaning an upper portion of a sheath associated with the sensor to prevent the soot from causing seizure of the sensor.

6. A multi-port probe calibration system, comprising:
a gas sensor having an active element; and
multiple ports configured for delivering focused calibration gases at the active element of the gas sensor from multiple directions that surround the active element of the gas sensor.

7. The system of claim 6, wherein the gas sensor is a gas analyzer.

8. The system of claim 6, wherein the calibration gases is zero and span gases.

9. The system of claim 6, wherein the multiple ports includes three ports, each port configured to deliver the calibration gases from one of the multiple directions to the active element of the gas sensor.

10. The system of claim 6, wherein the multiple ports includes six ports, each port configured to deliver the calibration gases from one of the multiple directions to the active element of the gas sensor.

11. The system of claim 6, wherein the multiple ports is interfaced to a sheath of the gas sensor and the sheath is flooded with the calibration gases to purge soot accumulated at the active element of the gas sensor.

12. A multi-port probe calibration system, comprising:
a sensor; and
a sheath configured with channels or holes at a tip of the sheath that surround a tip of the sensor, the sheath further configured to deliver focused calibration gases through the channels or holes at the tip of the sheath to the tip of the sensor to calibrate the sensor.

13. The system of claim 12, wherein the sheath includes 3 channels or holes.

14. The system of claim 12, wherein the sheath includes 6 channels or holes.

15. The system of claim 12, wherein the channel or holes surround the tip of the sensor from multiple directions and are configured to saturate the tip of the sensor by focusing the calibration gases on the tip of the sensor from the multiple directions to calibrate the sensor.

* * * * *